(12) United States Patent
Chung et al.

(10) Patent No.: US 7,933,019 B2
(45) Date of Patent: Apr. 26, 2011

(54) SURFACE PLASMON RESONANCE SENSOR USING ROTATING MIRROR

(75) Inventors: Bong-Hyun Chung, Daejeon (KR); Yong-Beom Shin, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/671,841

(22) PCT Filed: Aug. 13, 2008

(86) PCT No.: PCT/KR2008/004701
§ 371 (c)(1),
(2), (4) Date: Feb. 2, 2010

(87) PCT Pub. No.: WO2009/025465
PCT Pub. Date: Feb. 26, 2009

(65) Prior Publication Data
US 2010/0231914 A1    Sep. 16, 2010

(30) Foreign Application Priority Data

Aug. 20, 2007  (KR) .................. 10-2007-0083394

(51) Int. Cl.
*G01N 21/55* (2006.01)
(52) U.S. Cl. ..................... 356/445; 356/446
(58) Field of Classification Search .......... 356/445–448, 356/369
See application file for complete search history.

(56) References Cited

U.S. PATENT DOCUMENTS

| | | | |
|---|---|---|---|
| 4,844,613 A * | 7/1989 | Batchelder et al. | 356/318 |
| 5,485,277 A | 1/1996 | Foster | |
| 6,330,062 B1 * | 12/2001 | Corn et al. | 356/445 |
| 6,340,448 B1 | 1/2002 | Naya et al. | |
| 6,421,128 B1 * | 7/2002 | Salamon et al. | 356/445 |
| 6,493,097 B1 * | 12/2002 | Ivarsson | 356/630 |
| 6,731,388 B1 * | 5/2004 | Simon et al. | 356/445 |
| 6,753,188 B2 | 6/2004 | Perkins et al. | |
| 6,807,323 B2 * | 10/2004 | Beom et al. | 385/12 |
| 7,339,681 B2 * | 3/2008 | Su et al. | 356/491 |

FOREIGN PATENT DOCUMENTS

JP    10-307141    11/1998

OTHER PUBLICATIONS

International Search Report PCT/KR2008/004701 dated Jan. 8, 2009, 2 pages. Written Opinion of the International Searching Authority PCT/KR2008/004701 dated Jan. 8, 2009, 2008, 3 pages.
K. Oda and M. Fukui, Instantaneous Observation of Angular Scan-Attenuated Total Reflection Spectra, Oct. 1, 1986, vol. 59, No. 5,6, Elsevier Science Publishers B.V., North Holland Physics Publishing Division, pp. 361-365.

* cited by examiner

*Primary Examiner* — Sang Nguyen
(74) *Attorney, Agent, or Firm* — Daly, Crowley, Mofford & Durkee, LLP (57) ABSTRACT

Disclosed is a surface plasmon resonance sensor having a rotating mirror, including (a) an incident light source unit for oscillating a laser as incident light; (b) a polarizer for polarizing the incident light; (c) a rotating mirror having cylindrical or planar shapes for reflecting the polarized incident light to radiate disk-shaped light; (d) a light shielding film for allowing part of the disk-shaped light to pass therethrough and located adjacent to the central axis of the rotating mirror; (e) a cylinder lens for focusing the light passed through the light shielding film thereon; (f) a metal thin film for receiving the light focused on the cylinder lens to generate surface plasmon resonance; (g) a dielectric medium provided under the metal thin film; and (h) a detector for detecting the light reflected from the metal thin film. This surface plasmon resonance sensor can solve conventional interference problems of a laser being used as a light source to obtain an image for measurement of angle and two-dimensional reflected light intensity, including the deterioration of the quality of the image and the variation in the intensity of light source depending on the position of incidence.

18 Claims, 6 Drawing Sheets

FIGURE 1

PRIOR ART

SURFACE PLASMON RESONANCE SENSOR USING ROTATING MIRROR

TECHNICAL FIELD

The present invention relates to sensors for use in sample analysis and applications thereof, and particularly to an apparatus for realizing the incident light source of a sensor using surface plasmon resonance (SPR).

BACKGROUND ART

Surface plasmon is a quantized oscillation of free electrons that propagates along the surface of a conductor such as a metal thin film. Surface plasmon is excited to cause resonance by incident light which enters a metal thin film through a dielectric medium such as a prism at an incident angle of not less than the critical angle of the dielectric medium. This phenomenon is referred to as SPR. The incident angle of incident light that causes SPR, namely, the resonance angle, is very sensitive to changes in the refractive index of a material closest to the metal thin film. SPR sensors developed based on the above principle have been widely used for, through changes in the refractive index of a material namely a sample disposed closest to the metal thin film, the quantitative and qualitative analysis of a sample or the measurement of thickness of a sample in thin film form.

Figure 1:
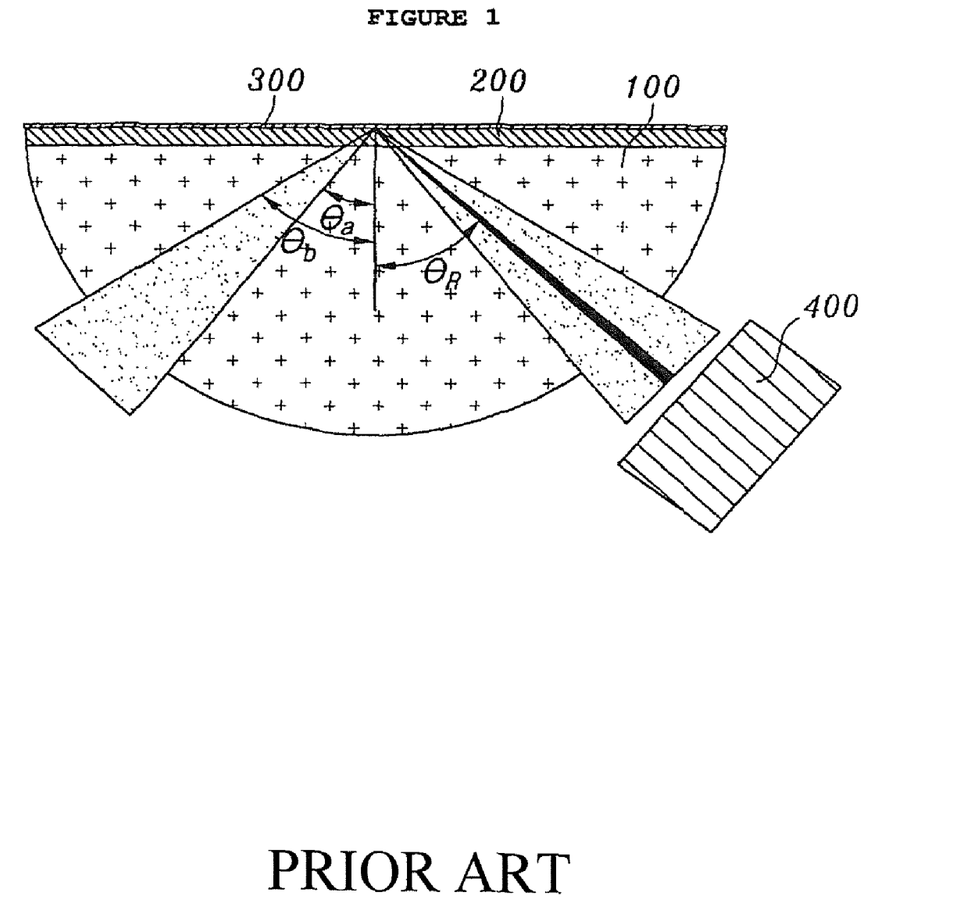
FIG. 1 schematically shows a process of measuring an angle using a conventional SPR sensor.

In the case where a Kretschmann configuration using a prism as illustrated in FIG. 1 is adopted to measure an angle in a SPR sensor, the angle is measured in a manner such that an incident light source of a single wavelength is focused on the center of a dielectric medium 100 and is then incident thereon in a predetermined angle range ($\theta_b \sim \theta_a$), after which the light reflected from a metal thin film 300 is detected using a multichannel photodetector 400 such as a charge coupled device (CCD) or a photodiode array, in which the reflected light is emitted in the same angle range as the incident light. As such, when a resonance angle ($\theta_R$) for SPR is present within the above angle range, the resonance angle at which the intensity of the reflected light is minimized and the area corresponding thereto is shown to be dark is measured in real time (U.S. Pat. No. 4,844,613). SPR sensor systems using the above method are actually commercially available from Biacore. In such a sensor system, a laser is mainly used as a light source but causes an interference problem, thus deteriorating the quality of the reflected light image. Accordingly, in a sensor system for accurate measurement of a resonance angle, hardware such as an electrical measurement unit requires high stability and precision, and a laser is thus unsuitable for use in small SPR sensor systems.

To overcome these problems, a luminescent diode (LED) having no interference may be used. However, this LED is disadvantageous because the LED light source which is not completely monochromatic but has a wavelength range of about 20~50 nm causes the angular spectrum of SPR to be broadened, and therefore the sensitivity of the sensor is reduced, undesirably requiring the additional use of a monochromatic filter.

Further, a method of using an oscillation mirror with the use of a point detector such as a photodiode and a laser is known. This method is based on a principle in which the oscillation mirror changes the incident angle depending on time, thus measuring the reflected light intensity depending on time, and the photodiode is synchronized with the oscillation mirror, thereby obtaining a function of the reflected light intensity with respect to the incident angle (Thijs Wink, Anal. Chem. 70, 827:832, 1998). However, this method is inadequate for application to small sensors because the oscillation mirror must be accurately synchronized with the photodiode in order to measure the reflected light intensity.

Korean Patent No. 407821 discloses a plasmon resonance sensor using upconversion of active ions, but is problematic in that incident light used therefor easily incurs an interference phenomenon and the light intensity is not uniform. Also, U.S. Pat. No. 6,798,521 discloses a SPR sensor using a flat mirror, but the incident light reflected from the flat mirror has a non-uniform distribution, undesirably resulting in technical limitations in which the accuracy of results of sample measurement is decreased.

DISCLOSURE

Technical Problem

Leading to the present invention, intensive and thorough research aiming to solve the problems encountered in the prior art, carried out by the present inventors, resulted in the finding that, when a rotating mirror is provided in a SPR sensor and a laser which is typically used is reflected from the rotating mirror that rotates at a predetermined speed, the laser thus reflected causes minimum interference and has a maximally uniform two-dimensional light intensity distribution.

Accordingly, the present invention provides a SPR sensor having a rotating mirror.

Technical Solution

According to the present invention, a SPR sensor having a rotating mirror may comprise (a) an incident light source unit for oscillating a laser as incident light; (b) a polarizer for polarizing the incident light; (c) a rotating mirror having cylindrical or plane shapes for reflecting the polarized incident light to radiate disk-shaped light; (d) a light shielding film for allowing part of the disk-shaped light to pass therethrough and located adjacent to the central axis of the rotating mirror; (e) a cylinder lens for focusing the light passed through the light shielding film thereon; (f) a metal thin film for receiving the light focused on the cylinder lens to generate SPR; (g) a dielectric medium provided under the metal thin film; and (h) a detector for detecting the light reflected from the metal thin film.

Advantageous Effects

According to the present invention, the SPR sensor using a rotating mirror can solve problems of a laser used as a conventional incident light source in which the sensitivity of a sensor is lowered owing to laser interference, thereby realizing a simple precise measurement system without the additional use of high precision electrical measurement hardware or software. In addition, the SPR sensor system using an incident light source apparatus according to the present invention can be efficiently utilized for analysis of properties of chemical materials and biomaterials adsorbed on the surface thereof and can increase a precision attainment of which is problematic in a small SPR sensor system.

DESCRIPTION OF THE REFERENCE NUMERALS IN THE DRAWINGS

100: dielectric medium 200: transparent substrate
300: metal thin film 400: detector
500: incident light source unit
510: polarizer
511: laser beam 600: rotating mirror
601: half-cylindrical prism
602: metal coating
610: disk-shaped laser beam
611: fan-shaped laser beam
700: light shielding film 800: cylinder lens

BEST MODE

Hereinafter, a detailed description will be given of the present invention with reference to the accompanying drawings.

The present invention is directed to a SPR sensor having a rotating mirror, in which a laser acting as an incident light source is reflected to a metal thin film through the rotating mirror having a cylindrical shape and then the resonance angle for SPR of the laser reflected from the metal thin film is measured, thereby analyzing a sample. In particular, the present invention is characterized in that the rotating mirror having a cylindrical shape which rotates at a predetermined speed is provided so that laser interference which easily takes place due to short wave and straightness properties of laser is minimized and the uniformity of a two-dimensional light intensity distribution is maximized.

Figure 2:
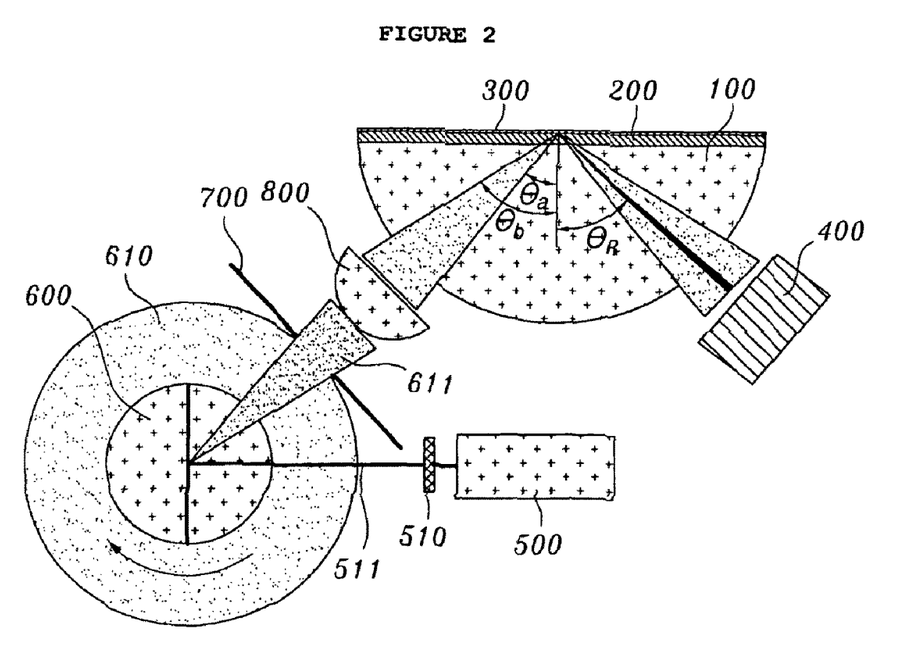
FIG. 2 schematically shows an apparatus for realizing an incident light source of a SPR sensor for measurement of an angle using a rotating mirror according to an embodiment of the present invention.

FIG. 2 schematically shows an apparatus for realizing the incident light source of the SPR sensor using the rotating mirror according to an embodiment of the present invention.

Examples of a sample to be analyzed using the SPR sensor having the rotating mirror according to the present invention include, but are not limited to, liquids, gases, and solids. Moreover, this sensor is very useful for the analysis of a biomaterial sample, in particular, an antibody, in which the sample is abutted or adsorbed on the metal thin film.

In the SPR sensor system according to the present invention, the use of a laser as an incident light source is preferable. A specific example of the incident light oscillated from an incident light source unit 500 includes a laser such as a laser diode (LD) and a gas laser. Examples of the form of the laser which is oscillated from the incident light source unit 500 include, but are not limited to, dots and lines. The laser having a wavelength of 400~900 nm is preferably used so as to optimize the generation of SPR on a metal thin film 300. If the wavelength of the laser is less than 400 nm, it is difficult to generate SPR. Conversely, if the wavelength exceeds 900 nm, it is difficult to obtain an image by means of the detector 400, and thus problems arise upon sample analysis.

Also, surface plasmon which occurs on the metal thin film 300 is excited only by a component parallel to the incident surface among incident light components, namely, a TM mode (Transverse Magnetic mode) polarized light component, and thus, the laser oscillated from the incident light source unit 500 is preferably converted into a TM mode using a polarizer 510 for forming TM polarized light.

The SPR sensor of the present invention is characterized in that it is provided with the rotating mirror 600 which rotates at a predetermined speed. Hence, the rotating mirror 600 which is used to reflect the incident light oscillated from the incident light source 500 so as to produce disk-shaped light should be rotated at a speed of 24 frames per second, specifically, about 1500 rpm or more. However, if the rotation speed exceeds 10000 rpm, the rotating mirror increasingly vibrates and becomes unstable. Therefore, it is preferred that the rotating mirror 600 be rotated at a speed of 1500~10000 rpm.

Figure 3:
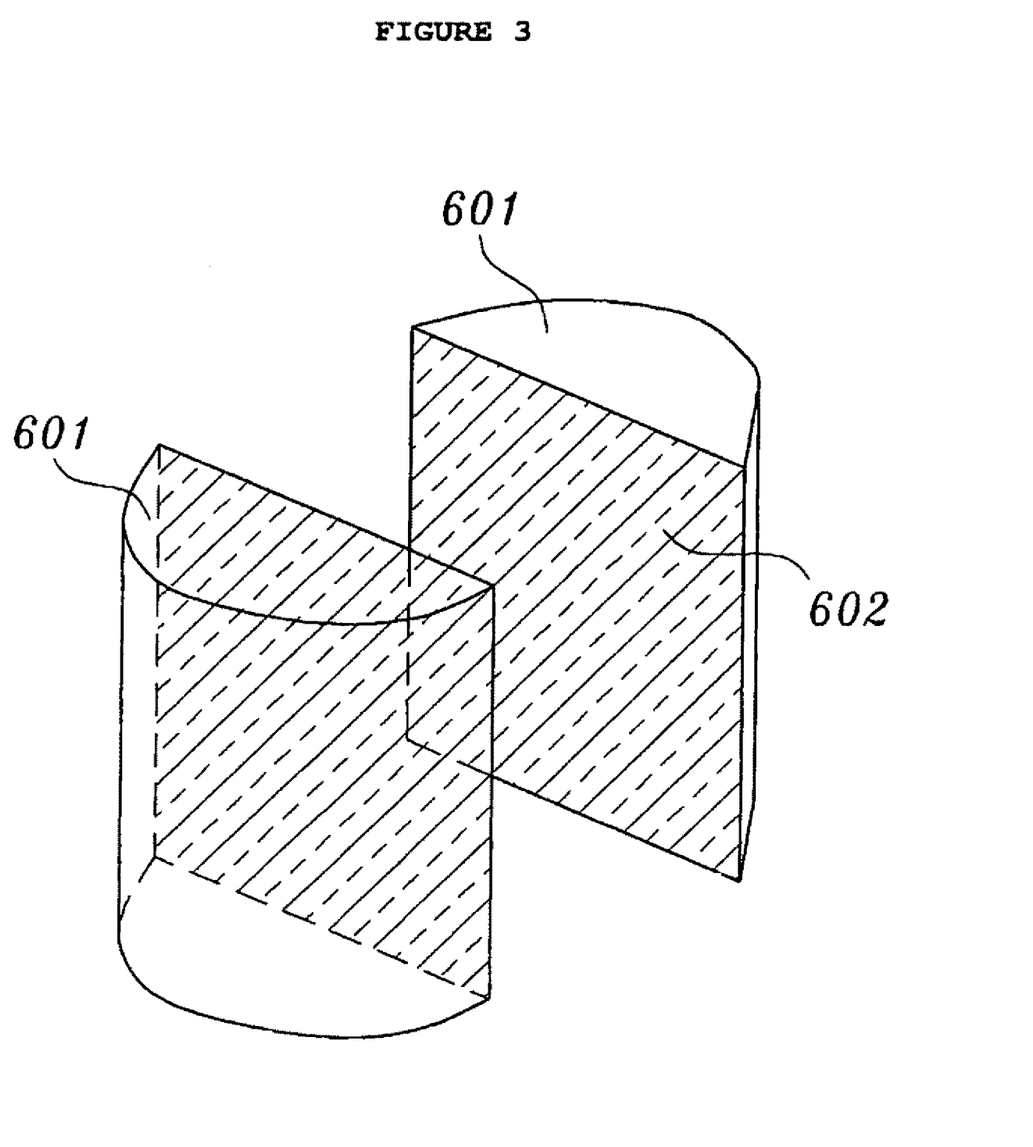
FIG. 3 shows the structure of the rotating mirror which is a main element for converting the incident light source according to the present invention.

Also, in the present invention, the rotating mirror 600 may have cylindrical shapes as illustrated in FIG. 3 in order to minimize the rotation load caused by air resistance upon rotation of the mirror and the instability of the measurement system due to the flow of air. The rotating mirror 600 having a cylindrical shape is manufactured by subjecting the flat surface of either of two half-cylindrical prisms 601 to metal coating 602 and then adhering the flat surfaces of the two prisms to face each other. The metal coating is applied on the flat surface of either of the two half-cylindrical prisms so as to reflect the laser beam 511 at all angles, and examples of the metal usable for the metal coating include silver, aluminum, chromium, and nickel, which are typically used for mirror. An adhesive for adhering the two half-cylindrical prisms includes UV epoxy in a liquid phase. The UV epoxy is a transparent polymer material and is cured upon exposure to UV light. The central axis of the rotating mirror 600 having a cylindrical shape thus manufactured is aligned with the axis of a motor which is provided under the rotating mirror 600 having a cylindrical shape, after which they are connected to each other using an UV epoxy adhesive. Thereby, the rotating mirror 600 having a cylindrical shape can be rotated about the central axis of the lower end thereof at a desired speed using power of the motor. The rotating mirror 600 may also have a plane shape, and could be used when it is placed on the center of motor.

The rotating mirror 600 is formed using a material having the capability to completely reflect a laser. The size of the rotating mirror 600 is set as small as possible to the extent that it can still receive the laser beam 511, provided that the size of the rotating mirror is larger than the diameter of the laser beam 511. Typically, the rotating mirror 600 has a size of 5 mm~2 cm in width and 5 mm~2 cm in length. If the width or length of the rotating mirror 600 is less than 5 mm, it is not easy to handle the rotating mirror 600 upon connection with the rotational axis of the motor. Conversely, if the width or length of the rotating mirror 600 exceeds 2 cm, a load may be applied to the small motor upon rapid rotation due to the size of the rotating mirror 600.

The laser beam 511, which is oscillated in the form of a full line with straightness from the incident light source unit 500, is reflected from the center of the mirror 600 having a cylindrical shape which rotates at a speed of 1500~10000 rpm, after which the light thus reflected is observed with the naked eye or using an inexpensive CCD. Thereby, a disk-shaped laser beam 610 which is expanded from the center of the reflection surface of the rotating mirror can be seen to be produced.

In the present invention, a light shielding film 700 has slits for allowing only the part of the disk-shaped laser beam 610 reflected from the rotating mirror 600, specifically, a fan-shaped laser beam 611 to pass therethrough, and is located at a predetermined distance from the center of the rotating mirror 600. When the light shielding film 700 is located to be closer to the central axis of the rotating mirror 600, the total size of the sensor is advantageously reduced. The slits of the light shielding film 700 are disposed at predetermined intervals so that the angle between two long sides of the fan-shaped laser beam is less than about 10°, specifically, $\theta_b-\theta_a$ which is the incident angle of the laser beam focused on one position of the metal thin film 300 is 10° or less. Almost all of the samples may be detected when $\theta_b-\theta_a$ is less than 10°. If the $\theta_b-\theta_a$ exceeds 10°, resolution is undesirably lowered.

In the present invention, a cylinder lens 800 is disposed between the light shielding film 700 and a dielectric medium 100 and thus plays a role in passing the fan-shaped laser beam 611 passed through the slits of the light shielding film 700 therethrough so that it is focused on one position of the metal thin film 300, specifically, on the center of the axis of the dielectric medium 100.

In the present invention, the dielectric medium 100 is formed using a transparent material such as glass or plastics, such as silica ($SiO_2$), BK7, SF11, etc., in order to transmit the laser beam passed through the cylinder lens 800 in a half-cylindrical form. Examples of the form of the dielectric medium 100 include, but are not limited to, a half-cylindrical shape, a triangular prism shape, a rectangular parallelepiped shape, and a diffraction grating shape. Further, a transparent substrate 200 on which the metal thin film 300 is to be formed is located on the dielectric medium 100, and the dielectric medium 100 and the transparent substrate 200 are attached to each other through optical coupling. The optical coupling is realized by use of an index matching oil which functions to integrate the dielectric medium 100 with the transparent substrate 200 to regard these two members as one from which the laser beam is then reflected (U.S. Pat. No. 6,807,323).

Figure 4:
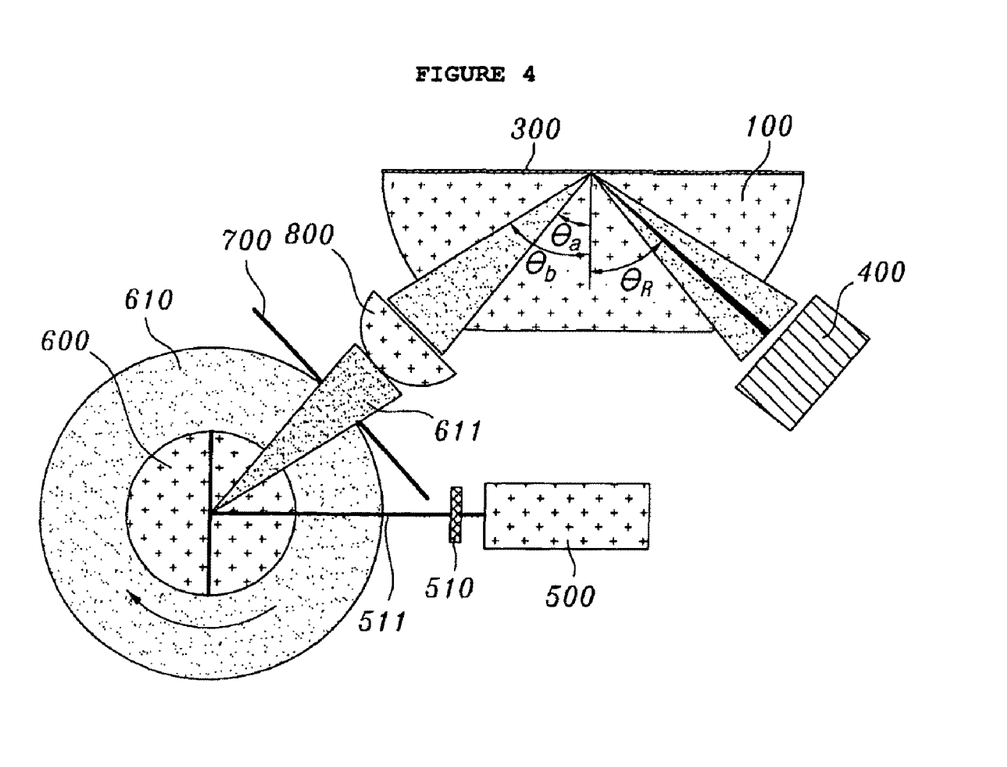
FIG. 4 schematically shows an apparatus for realizing an incident light source of a SPR sensor for measurement of an angle using a rotating mirror according to another embodiment of the present invention.

Alternatively, instead of using the transparent substrate 200, only a crossection of the half-cylindrical prism which is cut in a parallel direction with the metal thin film 300 may be used as a dielectric medium 100 (FIG. 4). Because the dielectric medium 100 reduces the wavelength of the laser beam incident thereon to thus increase a momentum, when the above laser beam is focused on the metal thin film 300, a SPR phenomenon is induced on the metal thin film 300.

In the present invention, the metal thin film 300 is foamed on the transparent substrate 200 on the dielectric medium 100 or is directly formed on the dielectric medium 100. Examples of the material for the metal thin film 300 include, but are not limited to, gold (Au), silver (Ag), and copper (Cu). On the metal thin film 300, SPR is generated by the incident light of the laser beam which is reflected from the rotating mirror 600, sequentially passed through the light shielding film 700 and the cylinder lens 800, and then focused on any one position of the metal thin film 300. Also, the metal thin film functions to reflect the incident light of the laser beam so that the reflected light of the laser beam is oscillated to the detector 400.

In the present invention, the detector 900 functions to monitor the dark portion of the image in which the intensity of light reflected from the metal thin film 300 at the same angle as $\theta_b-\theta_a$ is minimized, thus measuring the resonance angle ($\theta_R$) in real time, thereby analyzing the sample. The detector 400 for detecting the image includes an image detector, such as a photodiode array (PDA), a charge coupled device (CCD), and a complementary metal oxide semiconductor (CMOS).

In the SPR sensor having the rotating mirror 600 according to the present invention, the laser beam 511 oscillated from the incident light source unit 500 is polarized into a TM mode through the polarizer 510, after which the polarized laser beam 511 is reflected from the rotating mirror 600 having a cylindrical shape which rotates at a predetermined speed and is radiated into the disk-shaped laser beam 610. The disk-shaped laser beam 610 is passed through the light shielding film 700, thus obtaining the fan-shaped laser beam 611, which is then sequentially passed through the cylinder lens 800 and the dielectric medium 100 and subsequently focused on one position of the metal thin film 300. As such, SPR occurs on the metal thin film 300, the above laser beam is reflected from the metal thin film 300, and the resonance angle ($\theta_R$) which varies depending on the type of sample on the metal thin film 300 is measured by means of the detector 400, thereby analyzing the sample.

When the laser beam oscillated from the incident light source unit is in a dot form, the incident light reflected from the mirror having a cylindrical shape has a disk shape having the same thickness as the diameter of the dot of the incident light. On the other hand, when the incident light is in a line form having a predetermined length, the incident light reflected from the mirror having a cylindrical shape has a disk shape having the same thickness as the length of the line of the incident light. In the case where the incident light is in a line form, the line is preferably 1~20 mm long. If the length of the line is less than 1 mm, the number of samples to be analyzed is limited, thus making it impossible to analyze one or more samples. Conversely, if the length of the line exceeds 20 mm, limitations are imposed on assaying all of the samples using the detector.

The SPR sensor according to the present invention is advantageous because the interference of a laser used as an incident light source in a conventional SPR sensor is minimized and the uniformity of a two dimensional light intensity distribution is maximized, thanks to the use of the rotating mirror.

The interference indicates an interaction of light rays which are simultaneously reflected or refracted. In the present invention, such an interference phenomenon is minimized because light reflected from the rotating mirror can radially propagate around the rotating mirror, thus forming an average distribution.

Further, when the laser in a dot form is expanded, a two dimensional distribution in which the center of the expanded laser beam is bright and the peripheral portion thereof is dark, called a Gaussian distribution, is formed. When such a laser is reflected using the rotating mirror of the present invention, it is equally distributed in a rotation direction, thus maximizing the uniformity of a two dimensional light intensity distribution.

MODE FOR INVENTION

A better understanding of the present invention may be obtained through the following examples which are set forth to illustrate, but are not to be construed to limit the present invention.

EXAMPLE 1

Measurement of SPR by SPR Sensor Using Rotating Mirror 1

As a sample, a monolayer of mercapto-undecanol was adsorbed on a metal thin film on a transparent substrate, after which the transparent substrate was coupled to a dielectric medium using an index matching oil. As incident light, a diode laser beam having a length of 3 mm and a wavelength of 780 nm was used. The laser beam was converted into a TM mode through a polarizer and was then incident on a rotating mirror having a cylindrical shape. As such, the rotating mirror having a cylindrical shape was manufactured by subjecting the flat surface of either of two half-cylindrical prisms having a diameter of 1 cm and a height of 0.7 cm to aluminum coating and then adhering the aluminum-coated half-cylindrical prism to the other half-cylindrical prism not subjected to aluminum coating using liquid UV epoxy. A motor was disposed under the rotating mirror having a cylindrical shape so that the central axis thereof was aligned with the central axis of the rotating mirror, after which the rotating mirror and the motor were connected using UV epoxy.

Using the motor, the mirror having a cylindrical shape was rotated at a speed of 1500 rpm, and the laser beam incident on the rotating mirror was confirmed to be radiated in the form of a disk. The disk-shaped light was passed through a light shielding film located at a distance of 0.7 cm from the axis of the rotating mirror and having slits at intervals of 3 mm, thus obtaining a fan-shaped laser beam.

The fan-shaped laser beam was passed through a cylinder lens in lens combination of half-cylindrical form located at a distance of 1 cm from the light shielding film and then entered a dielectric medium in a half-cylindrical form made of BK7. The fan-shaped laser beam passed through the dielectric medium was incident on the metal thin film formed of gold positioned on the top of the dielectric medium, and was then reflected at the same angle as the incident angle. The resonance angle was measured using a CCD as a detector, thus analyzing the sample.

EXAMPLE 2

Measurement of SPR by SPR Sensor Using Rotating Mirror 2

Figure 5:
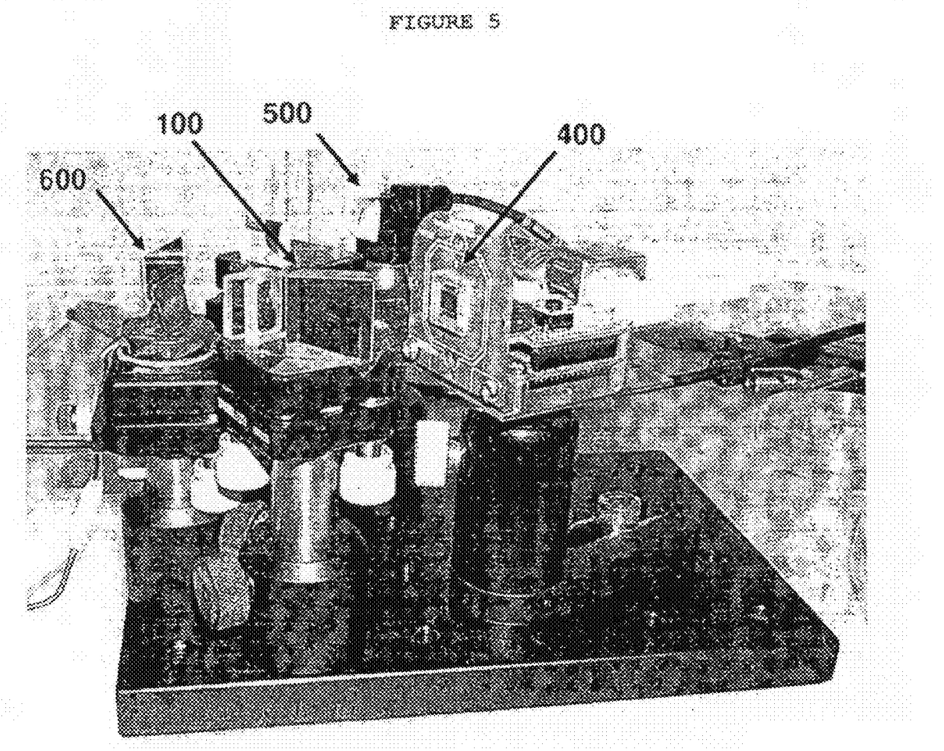
FIG. 5 shows an actual apparatus for realizing the incident light source of the SPR sensor for measurement of an angle using a rotating mirror according to the present invention.
Figure 6:
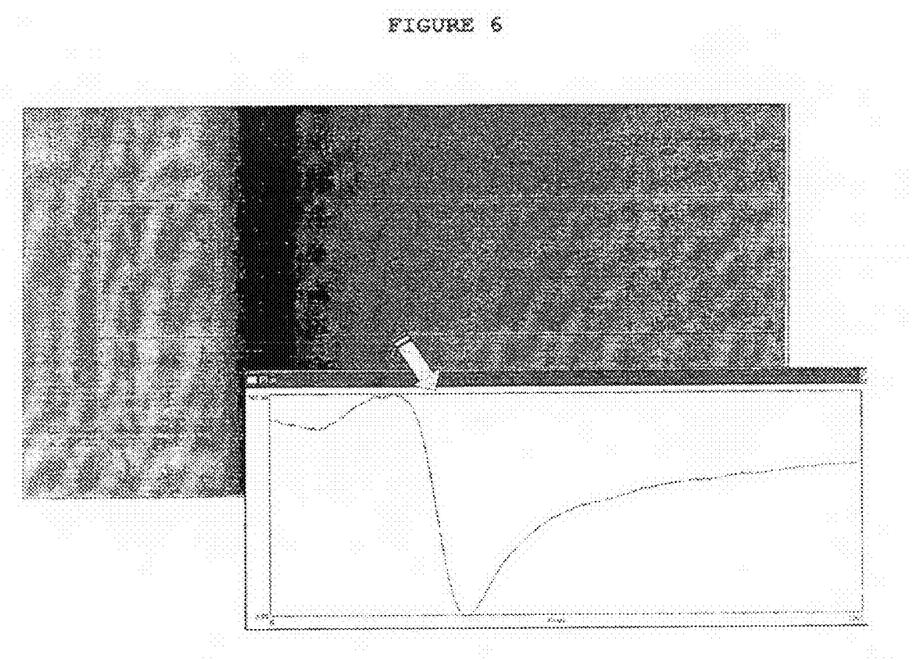
FIG. 6 shows a SPR spectrum measured using the apparatus according to the present invention.

The resonance angle for SPR was measured in the same manner as in Example 1, with the exception that a metal thin film was directly applied on a dielectric medium. This process is schematically illustrated in FIG. 4, and the actual apparatus thereof is shown in FIG. 5. Also, the SPR spectrum measured using the above apparatus is shown in FIG. 6.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A surface plasmon resonance sensor having a rotating mirror, comprising:
   (a) an incident light source unit for oscillating a laser as incident light;
   (b) a polarizer for polarizing the incident light;
   (c) a rotating mirror having cylindrical or plane shapes for reflecting the polarized incident light to radiate disk-shaped light, wherein the (c) rotating mirror having a cylindrical shape is manufactured by adhering two half-cylindrical prisms, in which a flat surface of either of the two half-cylindrical prisms is coated with a metal;
   (d) a light shielding film for allowing part of the disk-shaped light to pass therethrough and located adjacent to a central axis of the rotating mirror;
   (e) a cylinder lens for focusing the light passed through the light shielding film thereon;
   (f) a metal thin film for receiving the light focused on the cylinder lens to generate surface plasmon resonance;
   (g) a dielectric medium provided under the metal thin film; and
   (h) a detector for detecting an image corresponding to a minimal intensity of the light reflected from the metal thin film, thereby measuring a resonance angle in real time.

2. The sensor according to claim 1, wherein the incident light of (a) is a gas laser or a laser diode.

3. The sensor according to claim 1, wherein the incident light of (a) is in a dot form or in a line form.

4. The sensor according to claim 1, wherein the incident light of (a) is in a dot form, and the incident light reflected from the rotating mirror has a disk shape having a thickness equal to a diameter of the dot of the incident light.

5. The sensor according to claim 1, wherein the incident light of (a) is in a line form, and the incident light reflected from the rotating minor has a disk shape having a thickness equal to a length of the line of the incident light.

6. The sensor according to claim 5, wherein the length of the line is 1 mm~20 mm.

7. The sensor according to claim 1, wherein the (b) polarizer functions to convert the incident light into a transverse magnetic mode.

8. The sensor according to claim 1, wherein the (c) rotating mirror having a cylindrical shape has a size in which each of a width and a length is 5 mm~2 cm.

9. The sensor according to claim 1, wherein the metal is any one selected from the group consisting of silver, aluminum, chromium, and nickel.

10. The sensor according to claim 1, wherein the (c) rotating minor having a cylindrical shape is rotated at a speed of 1500-10000 rpm.

11. The sensor according to claim 1, wherein the (d) light shielding film has slits at intervals for $\theta b - \theta a \leq 10°$.

12. The sensor according to claim 1, wherein the (e) cylinder lens is lens combination of cylindrical prism.

13. The sensor according to claim 1, wherein the metal of (f) is selected from the group consisting of gold (Au), silver (Ag), and copper (Cu).

14. The sensor according to claim 1, wherein the (g) dielectric medium has a shape selected from the group consisting of a half-cylindrical shape, a triangular prism shape, a rectangular parallelepiped shape and a diffraction grating shape.

15. The sensor according to claim 1, wherein the (g) dielectric medium comprises a transparent material selected from the group consisting of glass and plastics.

16. The sensor according to claim 1, wherein the (h) detector is an image detector.

17. The sensor according to claim 16, wherein the image detector is any one selected from the group consisting of a photodiode array (PDA), a charge coupled device (CCD), and a complementary metal oxide semiconductor (CMOS).

18. The sensor according to claim 1, wherein a sample is abutted or adsorbed on the metal thin film.

* * * * *